(12) United States Patent
Akle et al.

(10) Patent No.: US 11,207,405 B2
(45) Date of Patent: *Dec. 28, 2021

(54) **CHECKPOINT INHIBITOR AND A WHOLE CELL *MYCOBACTERIUM* FOR USE IN CANCER THERAPY**

(71) Applicant: IMMODULON THERAPEUTICS LIMITED, Uxbridge (GB)

(72) Inventors: Charles Akle, Uxbridge (GB); Laura Rosa Brunet, Uxbridge (GB)

(73) Assignee: IMMODULON THERAPEUTICS LIMITED

( * ) Notice: Subject to any disclaimer, the term of this patent is extended or adjusted under 35 U.S.C. 154(b) by 442 days.

This patent is subject to a terminal disclaimer.

(21) Appl. No.: 15/738,674

(22) PCT Filed: Jun. 24, 2016

(86) PCT No.: PCT/GB2016/051893
§ 371 (c)(1),
(2) Date: Dec. 21, 2017

(87) PCT Pub. No.: WO2016/207646
PCT Pub. Date: Dec. 29, 2016

(65) Prior Publication Data
US 2018/0185479 A1 Jul. 5, 2018

(30) Foreign Application Priority Data

Jun. 24, 2015 (GB) .................................. 1511120
Jun. 24, 2015 (GB) .................................. 1511121

(51) Int. Cl.
*A61K 39/39* (2006.01)
*A61K 39/395* (2006.01)
*A61K 35/74* (2015.01)
*C07K 16/28* (2006.01)
*A61P 35/00* (2006.01)
*A61K 9/00* (2006.01)
*A61K 39/00* (2006.01)

(52) U.S. Cl.
CPC ...... *A61K 39/39558* (2013.01); *A61K 9/0019* (2013.01); *A61K 35/74* (2013.01); *A61P 35/00* (2018.01); *C07K 16/2827* (2013.01); *A61K 2039/505* (2013.01)

(58) Field of Classification Search
None
See application file for complete search history.

(56) References Cited

U.S. PATENT DOCUMENTS

| | | |
|---|---|---|
| 5,207,223 A | 5/1993 | Adler |
| 5,458,125 A | 10/1995 | Schweikard |
| 5,599,545 A | 2/1997 | Stanford et al. |
| 8,367,075 B2 | 2/2013 | Nandi et al. |
| 8,617,520 B2 * | 12/2013 | Akle ..................... A61K 45/06 424/184.1 |
| 10,610,577 B2 | 4/2020 | Alke et al. |
| 10,610,578 B2 | 4/2020 | Alke et al. |
| 2005/0187207 A1 | 8/2005 | Curry et al. |
| 2006/0110383 A1* | 5/2006 | Honjo .................... C12Q 1/025 424/133.1 |
| 2008/0318252 A1 | 12/2008 | Kachlany |
| 2009/0304749 A1 | 12/2009 | Stanford et al. |
| 2013/0004456 A1 | 1/2013 | Weinschenk et al. |
| 2013/0209517 A1 | 8/2013 | Akle et al. |
| 2014/0018606 A1 | 1/2014 | Raman et al. |
| 2015/0284416 A1* | 10/2015 | Zhao ....................... C07F 9/572 424/181.1 |
| 2017/0007693 A1* | 1/2017 | Weiner ................. A61K 9/0009 |
| 2019/0224294 A1 | 7/2019 | Akle et al. |
| 2020/0215175 A1 | 7/2020 | Akle et al. |
| 2020/0215176 A1 | 7/2020 | Akle et al. |
| 2020/0338181 A1 | 10/2020 | Akle et al. |

FOREIGN PATENT DOCUMENTS

| | | |
|---|---|---|
| EP | 2620159 | 7/2013 |
| WO | WO 00/64476 A2 | 11/2000 |
| WO | WO 03/049751 A1 | 6/2003 |
| WO | WO 2004/006837 A2 | 1/2004 |
| WO | WO 2007/050405 | 5/2007 |
| WO | WO 2007/071978 A1 | 6/2007 |
| WO | WO 2007/112316 A2 | 10/2007 |
| WO | WO 2008/110491 A2 | 9/2008 |
| WO | WO 2008/156712 A1 | 12/2008 |

(Continued)

OTHER PUBLICATIONS

Powles et al. (Journal of Clinical Oncology, 2014, abstract 5011) (Year: 2014).*
Patnaik et al. (Clinical Cancer Research, 21(19): 4286-4293, 2015).*
Cananzi, F.C.M. et al. "Long-term survival and outcome of patients originally given *Mycobacterium vaccae* for metastatic malignant melanoma" *Human Vaccines & Immunotherapeutics*, 2013, 9(11):2427-2433.
Houot, R. and Levy, R. "T-cell modulation combined with intratumoral CpG cures lymphoma in a mouse model without the need for chemotherapy" *Blood*, 2009, 113:3546-3552.
Maverakis, E. et al. "Metastatic Melanoma—A Review of Current and Future Treatment Options" *Acta Derm Venereol.*, 2015, 95:516-524.
O'Brien, M. et al. "A randomized phase II study of SRL172 (*Mycobacterium vaccae*) combined with chemotherapy in patients with advanced inoperable non-small-cell lung cancer and mesothelioma" *Br. J. Cancer*, 2000, 83(7):853-857.

(Continued)

*Primary Examiner* — Nelson B Moseley, II
(74) *Attorney, Agent, or Firm* — Saliwanchik, LLoyd & Eisenschenk (57) ABSTRACT

An immunomodulator for use in the treatment, reduction, inhibition or control of a neoplastic disease in a patient intended to undergo checkpoint inhibition therapy, selected from a cell, protein, peptide, antibody or antigen binding fragment thereof, directed against CTLA-4, PD-1, PD-L1 and combinations thereof, simultaneously, separately or sequentially with administration of the immunomodulator. The immunomodulator comprises a whole cell *Mycobacterium*, for example, *M. vaccae* or *M. obuense*.

18 Claims, 3 Drawing Sheets

(56) References Cited

FOREIGN PATENT DOCUMENTS

| WO | WO 2012/177624 A2 | 12/2012 |
| --- | --- | --- |
| WO | WO 2013/079980 A1 | 6/2013 |
| WO | WO 2013/114367 A2 | 8/2013 |
| WO | WO 2014/181121 | 11/2014 |
| WO | WO 2015/092382 | 6/2015 |
| WO | WO 2020/002905 | 1/2020 |

OTHER PUBLICATIONS

Zamarin, D. et al. "Localized oncolytic virotherapy overcomes systemic tumor resistance to immune checkpoint blockade immunotherapy" *Sci. Transl. Med.*, 2014, 6(226):226ra32.

Al, M. et al. "Immune checkpoint combinations from mouse toman" *Cancer Immunol Immunother*, 2015, pp. 885-892, vol. 64.

Crooks, J. et al., "The effects of combination treatment of IMM-101, a heat-killed whole cell preparation of *Mycobacterium obuense* (NCTC 13365) with checkpoint inhibitors in pre-clinical models," *31st Annual Meeting, Society for Immunotherapy of Cancer*, Poster No. 240, p. 1, (2016).

Crooks, J. et al., Abstract of "The effects of combination treatment of IMM-101, a heat-killed whole cell preparation of *Mycobacterium obuense* (NOTO 13365) with checkpoint inhibitors in pre-clinical models," *J. for ImmunoTherapy of Cancer*, 4 (Suppl 1): P233 (2016).

Dalgleish, A. et al., "Enhanced effect of checkpoint inhibitors when given after or together with IMM-101: significant responses in four advanced melanoma patients with No. additional major toxicity," *J. Transl. Med.* 16:227, pp. 1-7, (2018).

Dalgleish, A. et al., Abstract of "Five year survival in patients with metastatic melanoma receiving IMM-101," *Annals of Oncology* 26(Suppl 8): 5-14, pp. 1-2, (2015).

Dalgleish, A. et al., "Does IMM-101 prime for increased clinical responses to checkpoint inhibitors in metastatic melanoma and pancreatic cancer?" *31st Annual Meeting, Society for Immunotherapy of Cancer*, Poster No. 204, p. 1, (2016).

Dalgleish, A. et al., "Randomised, open-label, phase II study of gemcitabine with and without IMM-101 for advanced pancreatic cancer," *Brit. J. of Cancer* 115:789-796 (2016).

Hrouda, D. et al., "Allogeneic whole-tumour cell vaccination in the rat model of prostate cancer," *BJU International*, vol. 86, No. 6, Oct. 2000, pp. 742-748. ISSN: 1464-4096.

International Search Report and Written Opinion for corresponding International Patent Application No. PCT/GB2016/051893, dated Jan. 29, 2016, 11 pages.

International Preliminary Report on Patentability, PCT Application No. PCT/GB2012/052992, dated Jan. 24, 2014, 7 pages.

Ma, X. et al., "Combination sonodynamic therapy with immunoadjuvant may be a promising new modality for cancer treatment," *Medical Hypotheses, Eden Press*, vol. 72, No. 4, Apr. 2009, pp. 418-420, XP025964824, ISSN: 0306-9877.

Oka, H, et al., "Z-100, an immunomodulatory arabinomannan extracted from *Mycobacterium tuberculosis* strain Aoyama B, augments anti-tumor activities of X-ray irradiation against B16 melanoma in association with the improvement of type 1T cell responses," *Biological & Pharmaceutical Bulletin*, vol. 27, No. 1, Jan. 2004, pp. 82-88, XP002691872, ISSN:0918-6158.

Sur, P.K. et al., "Role of *Mycobacterium* was adjuvant treatment of lung cancer (non-small cell lung cancer),"*Journal of the Indian Medical Association, Indian Medical Association*, Calcutta, IN, vol. 101, No. 2, Feb. 2003, p. 118,120, XP009115704, ISSN:0019-5847.

Center for Drug Evaluation and Research, "BLA Multidisciplinary Review and Evaluation: BLA 761049 Bavencio (Avelumab)," Reference ID: 4073902, Feb. 2016, 194 pages.

Center for Drug Evaluation and Research, "Imfinzi CDER Pharmacology and Biopharmaceutics Review," Reference ID 4065384, Clinical Pharmacoloqv and Biopharmaceutics Review(s), Mar. 2017, 49 pages.

Center for Drug Evaluation and Research, "Yervoy CDER Pharmacology Review," Reference ID 125377, Clinical Pharmacology and Biopharmaceutics Review(s), Mar. 2011, 131 pages.

Food and Drug Administration, "Highlights of Prescribing Information: KEYTRUDA," Medication Guide, Reference ID 4449844, Jun. 2019, 80 pages.

Food and Drug Administration, "Highlights of Prescribing Information: OPDIVO," Medication Guide, Reference ID 4427750, May 2019, 78 pages.

Food and Drug Administration, "Highlights of Prescribing Information: YERVOY," Medication Guide, Reference ID 4430687, May 2019, 52 pages.

Food and Drug Administration, "Highlights of Prescribing Information: TECENTRIQ," Medication Guide, Reference ID 4000525, Oct. 2016, 23 pages.

Food and Drug Administration, "Highlights of Prescribing Information: BAVENCIO," Medical Guide, Reference ID 4095102, May 2017, 25 pages.

Food and Drug Administration, "Highlights of Prescribing Information: IMFINZI," Medical Guide, Reference ID 4223035, Feb. 2018, 27 pages.

International Search Report and Written Opinion for corresponding International Patent Application No. PCT/GB2016/051893, dated Dec. 29, 2016, 12 pages.

Ricks, T.K., "Tecentriq CDER Pharmacology Review," Center for Drug Evaluation and Research, Reference ID 3920269, BLA # 761034, Apr. 2016, 58 pages.

United States Office Action, U.S. Appl. No. 15/104,890, dated Apr. 24, 2018, 12 pages.

United States Office Action, U.S. Appl. No. 15/104,890, dated Aug. 30, 2017, 7 pages.

United States Office Action, U.S. Appl. No. 15/104,890, dated Feb. 15, 2019, 15 pages.

United States Office Action, U.S. Appl. No. 15/104,890, dated Jan. 9, 2017, 22 pages.

United States Office Action, U.S. Appl. No. 15/104,890, dated May 22, 2017, 10 pages.

Weis, S.L. et al., "Opdivo CDER Pharmacology Review," *Center for Drug Evaluation and Research*, Reference ID: 3667795, Dec. 2014, 99 pages.

Weis, S.L., "Keytruda CDER Pharmacology Review," Center for Drug Evaluation and Research, Reference ID: 3601748, Aug. 2014, 97 pages.

Wong, K.P. et al., "Effects of Administration Route, Dietary Condition, and Blood Glucose Level on Kinetics and Uptake of 18F-FDG in Mice," The Journal of Nuclear Medicine, May 2011, vol. 52, No. 5, 9 pages.

Zahalka, E., "Imfinzi CDER Pharmacology Review," Center for Drug Evaluation and Research, Reference ID 4070413, BLA#761069, Mar. 2017, 70 pages.

International Search Report and Written Opinion for corresponding International Patent Application No. PCT/GB2014/053717, dated Mar. 10, 2015, 14 pages.

Fowler, D. et al: "A heat-killed preparation of *Mycobacterium obuense* can reduce metastatic burden in vivo", *Journal for Immunotherapy of Cancer, Biomed Central Ltd*, London, UK, vol. 2, No. Suppl 3, Nov. 6, 2014 {Nov. 6, 2014), p. 54, XP021202569, ISSN: 2051-1426.

Stebbing J. et al: "An intra-patient placebo-controlled phase I trial to evaluate the safety and tolerability of intradermal IMM-101 in melanoma", *Annals of Oncology*, Oxford University Press, GB, vol. 23, No. 5, May 1, J012 {May 1, 2012), pp. 1314-1319, XP008159930, ISSN: 1569-8041.

Elia, A. et al. "Treatment with IMM-101 induces protective CD8+ T cell responses in clinically relevant models of pancreatic cancer", *Journal for ImmunoTherapy of Cancer*, 1 (Suppl 1): p. 215 (2013).

Fowler, D. W. et al. "Mycobacteriaactivategamma-deltaT-cellantitumour responses viacytokines fromtype 1 myeloid dendritic cells: a mechanism of action for cancer immunotherapy", *Cancer Immunol Immunotherapy*, 61:535-547 (2012).

Pending claims in U.S. Appl. No. 16/819,927, Mar. 24, 2020, pp. 1-3.

(56) References Cited

OTHER PUBLICATIONS

Pending claims in U.S. Appl. No. 16/820,058, Mar. 24, 2020, pp. 1-3.
Pending claims in U.S. Appl. No. 16/820,132, Mar. 24, 2020, pp. 1-3.
Pending claims in U.S. Appl. No. 16/916,194, Jul. 1, 2020, pp. 1.
Costa Neves, M. et al. "Extended Survival after Complete Pathological Response in Metastatic Pancreatic Ductal Adenocarcinoma Following Induction Chemotherapy, Chemoradiotherapy, and a Novel Immunotherapy Agent, IMM-101", *Cureus*, Dec. 26, 2015, 7(12):e435.
Declaration of Angus G. Dalgleish, M.D., under 37 CFR §1.132, dated Dec. 19, 2018, submitted in U.S. Appl. No. 15/104,890.
Den Brok, M.H.M.G.M. , et al., "Efficient loading of dentritic cells following cryo and radiofrequency ablation in combination with immune modulation induces anti-tumor immunity", British Journal of Cancer vol. 95, 2006, 896-905.
Final Office Action in U.S. Appl. No. 14/361,992 dated Aug. 16, 2017, 16 pages.
Final Office Action in U.S. Appl. No. 14/361,992 dated Jul. 5, 2016, 10 pages.
Finkelstein, Steven Eric, et al., "The Confluence of Stereotactic Ablative Radiotherapy and Tumor Immunology", Clinical and Developmental Immunology, vol. 2011, Article ID: 439752, doi: 10/11552011/439752, 2011, 1-7.
Gameiro, S. et al. "Combination therapy with local radiofrequency ablation and systemic vaccine enhances antitumor immunity and mediates local and distal tumor regression" *PLOS One*, 2013, 8:e70417, pp. 1-13.
International Search Report and Written Opinion for PCT/GB2016/051893 (WO 2016/207646) dated Sep. 15, 2016.
Napoletano, Chiara, et al., "RFA strongly modulates the immune syste and anti-tumor immune responses in metastatic liver patients", International Journal of Oncology, vol. 32, 2008, 481-490.
Non-Final Office Action in U.S. Appl. No. 14/361,992 dated Apr. 3, 2017, 8 pages.
Non-Final Office Action in U.S. Appl. No. 14/361,992 dated Jun. 28, 2018, 12 pages.
Non-Final Office Action in U.S. Appl. No. 14/361,992 dated Nov. 6, 2015, 8 pages.
PCT International Search Report in PCT/GB2012/052992, dated Mar. 1, 2013, 5 pages.
Pending claims in U.S. Appl. No. 16/916,194, Jun. 30, 2020, pp. 1.
Richards, S. "Internal pressure makes pancreatic tumors hard to treat" *Fred Hutch News Service*, May 10, 2016, pp. 1-5.
Study protocol information for Phase II Clinical Trial NCT01303172 from ClinicalTrials.Gov, downloaded Jun. 15, 2020.
Tesniere, A, et al., "Molecular characteristics of immunogenic cancer cell death", Cell Death and Differentiation vol. 15, 2008, 3-12.
Vakkila, Jukka, et al., "Inflammation and necrosis promote tumor growth", Nature Reviews: Immunology vol. 4, Aug. 2004,641-648.
Weledji, E. et al. "How grim is pancreatic cancer?" *Oncol. Rev.* 2016, 10:294, pp. 28-37.
Williams, Lynda, "Clonal evolution explains unpredictable leukemia disease course" medwireNews, Feb. 19, 2013, pp. 1-2.
Wolchok, J.D. et al. "Guidelines for the Evaluation of Immune Therapy Activity in Solid Tumors: Immune-Related Response Criteria" *Clin. Cancer Res.*, 2009, 15(23):7412-7420.
Zeh, III, Herbert J. , et al., "Addicted to Death—Invasive Cancer and the Immune Response to Unscheduled Cell Death", J. Immunother., vol. 28, No. 1, Jan./Feb. 2005, pp. 1-9, Abstract.
Zitvogel, Laurence , et al., "The anticancer immune response: indispensable for therapeutic success?", The Journal of Clinical Investigation vol. 118 No. 6, Jun. 2008, 1991-2001.
"Checkpoint inhibitor" definition on Wikipedia, "https://en.wikipedia.org/w/index.php?title=Checkpoint_inhibitor&oldid=990545057", retrieved Dec. 1, 2020.
Pardoll, D. "The blockade of immune checkpoints in cancer immunotherapy" *Nat. Rev. Cancer*, 2016, 12(4):252-264.

European Medicines Agency, Assessment report: atezolizumab, Jul. 20, 2017.
Ayaru, L. et al., "Unmasking of α-Fetoprotein-SpecificCD4+ T Cell Responses in Hepatocellular Carcinoma Patients Undergoing Embolization", *The Journal of Immunology*, 2007, 178:1914-1922.
Balkwill, F. et al., "Inflammation and cancer: back to Virchow?", *The Lancet: Review*, Feb. 17, 2001, 357:539-545.
Castano, A. et al., "Photodynamictherapy and anti-tumor immunity", *Nature Reviews: Cancer*, Jul. 2006, 6:535-545.
Dalgleish, A.G. "A multicenter randomized, open-label, proof-of-concept, phase II trial comparing gemcitabine with and without IMM-101 in advanced pancreatic cancer", *J. Oncology Suppl.* 336, 2015, 1 pg.
Den Brok, M.H.M.G.M. et al., "Synergy between In situ Cryoablation and TLR9 Stimulation Results in a Highly Effective In vivo Dentritic Cell Vaccine", *Cancer Res.*, Jul. 15, 2006, 66(14):7285-7292.
Dunn, G. et al., "The Three Es of Cancer Immunoediting", *Annu. Rev. Immunol.*, 2004, 22:329-360.
Dvorak, H., "Tumors: Wounds That Do Not Heal—Similarities between Tumor Stroma Generation and Wound Healing", *The New England Journal of Medicine*, Dec. 25, 1986, 315(26):1650-1659.
Hrouda, D. et al., "Immunotherapy of advanced prostate cancer: a phase I/II trial using *Mycobacterium vaccae* (SRL172)", *British Journal of Urology*, 1998, 82:568-573.
Jerome, K. et al., "The Danger Within", *The New England Journal of Medicine*, Jan. 22, 2004, vol. 350(4):411-412.
Korbelik, M. et al., "Enhancement of tumour response to photodynamic therapy by adjuvant *Mycobacterium* cell-wall treatment", *Journal of Photochemistry and Photobiology B: Biology*, 1998, 44:151-158.
Korbelik, M. et al., "Interaction Between Photodynamic Therapy and BCG Immunotherapy Responsible for the Reduced Recurrence of Treated Mouse Tumors", *Photochemistry and Photobiology*, 2001, 73 (4):403-409.
Kumar Sur, P. et al., "Role of *Mycobacterium* was Adjuvant Treatment of Lung Cancer (Non-small Cell Lung Cancer)", *J. Indian. Med. Assoc.*, Feb. 2003, 101 (2):118-120 (2 pages).
Morse, M. et al., "An Odd But Synergistic Couple: Immunotherapy Combined With Radiotherapy", *Cancer Network: Home of the Journal Oncology*, Aug. 1, 2008, 3 pages.
Schwartsburd, P.M., "Chronic inflammation as inductor of pro-cancer microenvironment: Pathogenesis of dysregulated feedback control", *Cancer and Metastasis Reviews*, 2003, 22:95-102.
Shankar, B. et al., "Modification of immune response by low dose ionizing radiation: role of apoptosis", *Immunology Letters*, 1999, 68:237-245.
Slaviero, K. et al., "Inflammatory response: an unrecognised source of variability in the pharmacokinetics and pharmacodynamics of cancer chemotherapy", *The Lancet: Oncology*, Apr. 2003, 4:224-232.
Tang, X. et al., "Design of Freeze-Drying Processes for Pharmaceuticals: Practical Advice", *Pharmaceutical Research*, Feb. 2004, 21 (2): 191-200, abstract.
Vogl, T.J. et al., "Activation of tumor-specific T lymphocytes after laser-induced thermotherapy in patients with colorectal liver metastases", *Cancer Immunol. Immunother.*, 2009, 58:1557-1563.
Yuk, J-M. et al., "Bacillus calmette-guerin cell wall cytoskeleton enhances colon cancer radiosensitivity through autophagy", *Autophagy*, vol. 6, Issue 1, Jan. 1, 2010, pp. 46-60.
Zerbini, A. et al., "Radiofrequency Thermal Ablation of Hepatocellular Carcinoma Liver Nodules Can Activate and Enhance Tumor-Specific T-Cell Responses", *Cancer Research*, Jan. 15, 2006, vol. 66(2):1139-1146.
Zitvogel, L. et al., "Immune Response Against Dying Tumor Cells", *Advances in Immunology*, 2004, 84:131-179.
"A phase II, single arm, investigative study of IMM-101 in combination with radiation induced tumour necrosis in patients with previously treated colorectal cancer" Study No. IMM-101-007 (Completed), Immodulon, Jun. 22, 2012, 2 pages.
"A Study of IMM-101 in combination with radiation induced tumour necrosis in colorectal cancer" ClinicalTrials Identifier NCT01539824, Feb. 28, 2012, 8 pages.

(56) References Cited

OTHER PUBLICATIONS

Gaya, A. "A phase II, single arm, investigative study of IMM-101 in combination with stereotactic radiotherapy-induced tumour necrosis in patients with previously treated colorectal cancer" The 2013 SRS/SBRT Scientific Meeting hosted by the Radiosurgery Society, Carlsbad, California, Feb. 21-23, 2013, Abstract.

Golden, E. and Formenti, S. "Radiation therapy and immunotherapy: Growing pains" *Int. J. Radiation Oncol. Biol. Phys.*, Feb. 2015, 91(2):252-254.

Mahadevan, A. et al. "Induction gemcitabine and stereotactic body radiotherapy for locally advanced nonmetastatic pancreas cancer" *Int. J. Radiation Oncol. Biol. Phys.*, 2011, 81(4):e615-e622.

Mahadevan, A. et al. "Stereotactic body radiotherapy and gemcitabine for locally advanced pancreatic cancer" *Int. J. Radiation Oncol. Biol. Phys.*, 2010, 78(3)735-742.

Schellenberg, D. et al. "Gemcitabine chemotherapy and single-fraction stereotactic body radiotherapy for locally advanced pancreatic cancer" *Int. J. Radiation Oncol. Biol. Phys.*, 2008, 72(3):678-686.

\* cited by examiner

Figure 3

CHECKPOINT INHIBITOR AND A WHOLE CELL *MYCOBACTERIUM* FOR USE IN CANCER THERAPY

CROSS-REFERENCE TO RELATED APPLICATION

This application is the National Stage of International Application Number PCT/GB2016/051893, filed Jun. 24, 2016, which is hereby incorporated by reference herein in its entirety, including any figures, tables, nucleic acid sequences, amino acid sequences, or drawings.

FIELD OF THE INVENTION

The present invention relates to the field of cancer therapy. In particular, the present invention relates to a method of preventing, treating or inhibiting the development of tumours and/or metastases in a subject.

BACKGROUND OF THE INVENTION

In humans with advance cancer, anti-tumour immunity is often ineffective due to the tightly regulated interplay of pro- and anti-inflammatory, immune-stimulatory and immuno-suppressive signals. For example, loss of the anti-inflammatory signals leads to chronic inflammation and prolonged proliferative signalling. Interestingly, cytokines that both promote and suppress proliferation of the tumour cells are produced at the tumour site. It is the imbalance between the effects of these various processes that results in tumour promotion.

To date, a major barrier to attempts to develop effective immunotherapy for cancer has been an inability to break immunosuppression at the cancer site and restore normal networks of immune reactivity. The physiological approach of immunotherapy is to normalize the immune reactivity so that, for example, the endogenous tumour antigens would be recognized and effective cytolytic responses would be developed against tumour cells. Although it was once unclear if tumour immunosurveillance existed, it is now believed that the immune system constantly monitors and eliminates newly transformed cells. Accordingly, cancer cells may alter their phenotype in response to immune pressure in order to escape attack (immunoediting) and upregulate expression of inhibitory signals. Through immunoediting and other subversive processes, primary tumour and metastasis maintain their own survival.

One of the major mechanisms of anti-tumour immunity subversion is known as 'T-cell exhaustion', which results from chronic exposure to antigens and is characterized by the up-regulation of inhibitory receptors. These inhibitory receptors serve as immune checkpoints in order to prevent uncontrolled immune reactions.

PD-1 and co-inhibitory receptors such as cytotoxic T-lymphocyte antigen 4 (CTLA-4, B and T Lymphocyte Attenuator (BTLA; CD272), T cell Immunoglobulin and Mucin domain-3 (Tim-3), Lymphocyte Activation Gene-3 (Lag-3; CD223), and others are often referred to as a checkpoint regulators. They act as molecular "tollbooths," which allow extracellular information to dictate whether cell cycle progression and other intracellular signalling processes should proceed.

In addition to specific antigen recognition through the TCR, T-cell activation is regulated through a balance of positive and negative signals provided by co-stimulatory receptors. These surface proteins are typically members of either the TNF receptor or B7 superfamilies. Agonistic antibodies directed against activating co-stimulatory molecules and blocking antibodies against negative co-stimulatory molecules may enhance T-cell stimulation to promote tumour destruction.

Programmed Cell Death Protein 1, (PD-1 or CD279), a 55-kD type 1 transmembrane protein, is a member of the CD28 family of T cell co-stimulatory receptors that include immunoglobulin superfamily member CD28, CTLA-4, inducible co-stimulator (ICOS), and BTLA. PD-1 is highly expressed on activated T cells and B cells. PD-1 expression can also be detected on memory T-cell subsets with variable levels of expression. Two ligands specific for PD-1 have been identified: programmed death-ligand 1 (PD-L1, also known as B7-H1 or CD274) and PD-L2 (also known as B7-DC or CD273). PD-L1 and PD-L2 have been shown to down-regulate T cell activation upon binding to PD-1 in both mouse and human systems (Okazaki et al., Int Immunol., 2007; 19: 813-824). The interaction of PD-1 with its ligands, PD-L1 and PD-L2, which are expressed on antigen-presenting cells (APCs) and dendritic cells (DCs), transmits negative regulatory stimuli to down-modulate the activated T cell immune response. Blockade of PD-1 suppresses this negative signal and amplifies T cell responses.

Numerous studies indicate that the cancer microenvironment manipulates the PD-L1-/PD-1 signalling pathway and that induction of PD-L1 expression is associated with inhibition of immune responses against cancer, thus permitting cancer progression and metastasis. The PD-L1/PD-1 signalling pathway is a primary mechanism of cancer immune evasion for several reasons. First, and most importantly, this pathway is involved in negative regulation of immune responses of activated T effector cells, found in the periphery. Second, PD-L1 is up-regulated in cancer microenvironments, while PD-1 is also up-regulated on activated tumour infiltrating T cells, thus possibly potentiating a vicious cycle of inhibition. Third, this pathway is intricately involved in both innate and adaptive immune regulation through bi-directional signalling. These factors make the PD-1/PD-L1 complex a central point through which cancer can manipulate immune responses and promote its own progression.

The first immune-checkpoint inhibitor to be tested in a clinical trial was ipilimumab (Yervoy, Bristol-Myers Squibb), a CTLA-4 mAb. CTLA-4 belongs to the immunoglobulin superfamily of receptors, which also includes PD-1, BTLA, TIM-3, and V-domain immunoglobulin suppressor of T cell activation (VISTA).

Anti-CTLA-4 mAb is a powerful checkpoint inhibitor which removes "the break" from both naïve and antigen-experienced cells. Therapy enhances the antitumor function of CD8+ T cells, increases the ratio of CD8+ T cells to Foxp3+T regulatory cells, and inhibits the suppressive function of T regulatory cells. The major drawback to anti-CTLA-4 mAb therapy is the generation of autoimmune toxicities due to on-target effects of an over-exuberant immune system which has lost the ability to turn itself down. It has been reported that up to 25% of patients treated with ipilimumab developed serious grade 3-4 adverse events/ autoimmune-type side effects including dermatitis, entero-colitis, hepatitis, endocrinopathies (including hypophysitis, thyroiditis, and adrenalitis), arthritis, uveitis, nephritis, and aseptic meningitis. In contrast to the anti-CTLA-4 experience, anti-PD-1 therapy appears to be better-tolerated and induces a relatively lower rate of autoimmune-type side effects.

TIM-3 has been identified as another important inhibitory receptor expressed by exhausted CD8+ T cells. In mouse models of cancer, it has been shown that the most dysfunctional tumour-infiltrating CD8+ T cells actually co-express PD-1 and TIM-3.

LAG-3 is another recently identified inhibitory receptor that acts to limit effector T-cell function and augment the suppressive activity of T regulatory cells. It has recently been revealed that PD-1 and LAG-3 are extensively co-expressed by tumour-infiltrating T cells in mice, and that combined blockade of PD-1 and LAG-3 provokes potent synergistic antitumor immune responses in mouse models of cancer.

PD-1 pathway blockade can be combined with vaccines or other immunomodulatory antibodies for improved therapeutic efficacy (Hirano, F. et al, Cancer Res., 65(3): 1089-1096 (2005); Li, B. et al, Clin. Cancer Res., 15: 1507-1509 (2009); and Curran, M. A. et al, Proc. Natl. Acad. Set, 107(9):4275-4280 (2010)).

Currently, antagonist mAbs against both PD-1 and their ligand PD-L1 are in various stages of development for the treatment of cancer, and recent human trials have shown promising results in cancer patients with advanced, treatment-refractory disease.

The first of the agents blocking the B7-H1/PD-1 pathway to enter phase I clinical trials was Nivolumab (MDX-1106/BMS-936558/ONO-4538), a fully human IgG4 anti-PD-1 mAb developed by Bristol-Myers Squibb. Another PD-1 mAb undergoing clinical evaluation is CT-011, a humanized IgG1 mAb specific for PD-1 developed by CureTech Ltd. Other agents include Lambrolizumab (MK-3475—Merck), a humanized monoclonal IgG4 PD-1 antibody; BMS-936559, a fully human IgG4 PD-L1 antibody and Roche's MPDL3280A, a human monoclonal antibody that targets the PD-L1 pathway.

The results of a phase II study that compared combined nivolumab and ipilimumab with ipilimumab alone in patients with BRAF wild-type melanoma showed objective response rates of 61% with the combination therapy and 11% with the monotherapy, with complete responses in 22% and 0% of patients, respectively. Treatment-related adverse events of grade 3 or 4 were reported in 54% of the patients in the combination group and in 24% of those in the ipilimumab group. Treatment-related adverse events of any grade that led to discontinuation of the study drug occurred in 7.7% of the patients in the nivolumab group, 36.4% of those in the nivolumab-plus-ipilimumab group, and 14.8% of those in the ipilimumab group.

Accordingly, an aim of the present invention is a combination therapy for treating cancer comprising an immunomodulator and blockade of checkpoint inhibitors with the potential to elicit potent and durable immune responses.

Another aim of the present invention is a combination therapy for treating cancer comprising an immunomodulator and blockade of checkpoint inhibitors with the potential to reduce treatment-related adverse events.

SUMMARY OF THE INVENTION

The present invention provides an effective method for treating and/or preventing cancer and/or the establishment of metastases by administering a checkpoint inhibitor which acts synergistically with a whole cell non-pathogenic heat-killed *Mycobacterium*.

In a first aspect of the invention, there is an immunomodulator for use in the treatment, reduction, inhibition or control of cancer in a patient intended to undergo checkpoint inhibition therapy, and wherein said checkpoint inhibition therapy comprises administration of a blocking agent, selected from a cell, protein, peptide, antibody or antigen binding fragment thereof, directed against CTLA-4, PD-1, PD-L1, PD-L2, LAG-3, B7-H3, B7-H4, B7-H6, A2AR, or IDO, and combinations thereof, wherein the immunomodulator comprises a whole cell, non-pathogenic heat-killed *Mycobacterium* and wherein said immunomodulator is to be administered simultaneously, separately or sequentially with administration of the checkpoint inhibition therapy, optionally wherein said checkpoint inhibition therapy comprises administration of a sub-therapeutic amount and/or duration of said blocking agent.

In a second aspect of the invention, there is a method of treating, reducing, inhibiting or controlling a neoplasia, tumour or cancer in a subject, wherein said method comprises simultaneously, separately or sequentially administering to the subject, (i) a checkpoint inhibitor, selected from a cell, protein, peptide, antibody or antigen binding fragment thereof, directed against CTLA-4, PD-1, PD-L1, PD-L2, LAG-3, B7-H3, B7-H4, B7-H6, A2AR, or IDO, and combinations thereof, and (ii) an immunomodulator, wherein said method results in enhanced therapeutic efficacy relative to administration of the checkpoint inhibitor or immunomodulator alone, and wherein the immunomodulator comprises a whole cell, non-pathogenic heat-killed *Mycobacterium*, and optionally wherein said method comprises administration of a sub-therapeutic amount of said checkpoint inhibitor.

The present invention therefore provides a combination therapy of checkpoint inhibitor therapy together with a specific type of immunotherapy comprising administration of an immunomodulator. The inventors have found that the combination of both therapies is synergistic beyond simple additive effects of each therapy used individually.

DESCRIPTION OF THE DRAWINGS

The invention is described with reference to the following drawings, in which.

DETAILED DESCRIPTION OF THE INVENTION

The invention provides a method for treating, reducing, inhibiting or controlling a neoplasia, tumour or cancer in a subject involving administering an immunomodulator and a checkpoint inhibitor. It is based upon the discovery that administration of an immunomodulator (whole cell heat-killed *Mycobacterium*) in combination with a checkpoint inhibitor directed against PD-L1, PD-1, CTLA-4, PD-L2, CAG-3, B7-H3, B7-H4, B7-H6, A2AR or IDO results in synergistic anti-tumour activity and/or antitumor activity that is more potent than administration of immunomodulator or checkpoint inhibitor alone.

It is preferred that the checkpoint inhibitor for use in the present invention is one directed against PD-L1, PD-1 or CTLA-4. For example, the inhibitor may be directed against PD-L1.

In order that the present invention may be more readily understood, certain terms are first defined. Additional definitions are set forth throughout the detailed description.

A "checkpoint inhibitor" is an agent which acts on surface proteins which are members of either the TNF receptor or B7 superfamilies, including agents which bind to negative co-stimulatory molecules selected from CTLA-4, PD-1, TIM-3, BTLA, VISTA, LAG-3, and/or their respective ligands, including PD-L1. (Mellman et al., supra). A "blocking agent" is an agent which either binds to the above co-stimulatory molecules and/or their respective ligands. "Checkpoint inhibitor" and "blocking agent" are used interchangeably throughout. The inhibitor is preferably an antibody or antigenic-binding molecule that targets an antigenic site on the surface proteins. For example, the inhibitor is an antibody that targets an antigenic site on PD-L1, or PD-1 or CTLA-4.

An immunomodulator, as defined according to the present invention, is a component which stimulates innate and type-1 immunity, including Th1 and macrophage activation and cytotoxic cell activity, as well as independently down-regulating inappropriate anti-Th2 responses via immuno-regulatory mechanisms.

The terms "tumour," "cancer" and "neoplasia" are used interchangeably and refer to a cell or population of cells whose growth, proliferation or survival is greater than growth, proliferation or survival of a normal counterpart cell, e.g. a cell proliferative or differentiative disorder. Typically, the growth is uncontrolled. The term "malignancy" refers to invasion of nearby tissue. The term "metastasis" refers to spread or dissemination of a tumour, cancer or neoplasia to other sites, locations or regions within the subject, in which the sites, locations or regions are distinct from the primary tumour or cancer.

The terms "Programmed Death 1," "Programmed Cell Death 1," "Protein PD-1," "PD-1," and "PD1," are used interchangeably, and include variants, isoforms, species homologs of human PD-1, and analogs having at least one common epitope with PD-1. The complete PD-1 sequence can be found under GenBank Accession No. U64863.

The terms "CD27," and "CD27 antigen" are used interchangeably, and include variants, isoforms, species homologs of human CD27, and analogs having at least one common epitope with CD27 (see, e.g., Hendriks (2000) *Nat Immunol.* 171 (5): 433-40.)

The terms "B7-H3" and "CD276" are used interchangeably, and include variants, isoforms, species homologs of human B7-H3, and analogs having at least one common epitope with B7-H3 (see e.g. Wilcox et al., (2012) *Eur. J. Haematology;* 88:465-475).

The terms "B7-H4" and "VTCN1" are used interchangeably, and include variants, isoforms, species homologs of human B7-H4, and analogs having at least one common epitope with B7-H4 (Wilcox supra).

The terms "A2AR" and "Adenosine A2A receptor" are used interchangeably, and include variants, isoforms, species homologs of human A2AR, and analogs having at least one common epitope with A2AR.

The terms "IDO" and "Indoleamine 2,3-dioxygenase" are used interchangeably, and include variants, isoforms, species homologs of human IDO, and analogs having at least one common epitope with IDO.

The terms "cytotoxic T lymphocyte-associated antigen-4," "CTLA-4," "CTLA4," and "CTLA-4 antigen" (see, e.g., Murata, Am. J. Pathol. (1999) 155:453-460) are used interchangeably, and include variants, isoforms, species homologs of human CTLA-4, and analogs having at least one common epitope with CTLA-4 (see, e.g., Balzano (1992) Int. J. Cancer Suppl. 7:28-32). The complete CTLA-4 nucleic acid sequence can be found under GenBank Accession No. L15006.

As used herein, "sub-therapeutic dose" means a dose of a therapeutic compound (e.g., an antibody) or duration of therapy which is lower than the usual or typical dose of the therapeutic compound or therapy of shorter duration, when administered alone for the treatment of cancer.

The term "therapeutically effective amount" is defined as an amount of a checkpoint inhibitor, in combination with an immunomodulator, that preferably results in a decrease in severity of disease symptoms, an increase in frequency and duration of disease symptom-free periods, or a prevention of impairment or disability due to the disease affliction. The terms "effective amount" or "pharmaceutically effective amount" refer to a sufficient amount of an agent to provide the desired biological or therapeutic result. That result can be reduction, amelioration, palliation, lessening, delaying, and/or alleviation of one or more of the signs, symptoms, or causes of a disease, or any other desired alteration of a biological system. In reference to cancer, an effective amount may comprise an amount sufficient to cause a tumour to shrink and/or to decrease the growth rate of the tumour (such as to suppress tumour growth) or to prevent or delay other unwanted cell proliferation. In some embodiments, an effective amount is an amount sufficient to delay development, or prolong survival or induce stabilisation of the cancer or tumour.

In some embodiments, a therapeutically effective amount is an amount sufficient to prevent or delay recurrence. A therapeutically effective amount can be administered in one or more administrations. The therapeutically effective amount of the drug or combination may result in one or more of the following: (i) reduce the number of cancer cells; (ii) reduce tumour size; (iii) inhibit, retard, slow to some extent and preferably stop cancer cell infiltration into peripheral organs; (iv) inhibit (i.e., slow to some extent and preferably stop) tumour metastasis; (v) inhibit tumour growth; (vi) prevent or delay occurrence and/or recurrence of tumour; and/or (vii) relieve to some extent one or more of the symptoms associated with the cancer.

For example, for the treatment of tumours, a "therapeutically effective dosage" may induce tumour shrinkage by at least about 5% relative to baseline measurement, such as at least about 10%, or about 20%, or about 60% or more. The baseline measurement may be derived from untreated subjects.

A therapeutically effective amount of a therapeutic compound can decrease tumour size, or otherwise ameliorate symptoms in a subject. One of ordinary skill in the art would be able to determine such amounts based on such factors as the subject's size, the severity of the subject's symptoms, and the particular composition or route of administration selected.

The term "immune response" refers to the action of, for example, lymphocytes, antigen presenting cells, phagocytic cells, granulocytes, and soluble macromolecules produced by the above cells or the liver (including antibodies, cytokines, and complement) that results in selective damage to, destruction of, or elimination from the human body of cancerous cells.

The term "antibody" as referred to herein includes whole antibodies and any antigen-binding fragment (i.e., "antigen-binding portion") or single chains thereof.

The term "antigen-binding portion" of an antibody (or simply "antibody portion"), as used herein, refers to one or more fragments of an antibody that retain the ability to specifically bind to a receptor and its ligand (e.g., PD-1). including: (i) a Fab fragment, (ii) a F(ab') 2 fragment, (iii) a Fd fragment consisting of the VH and CHI domains; (iv) a Fv fragment, (v) a dAb fragment (Ward et al, Nature, 341:544-546 (1989)), which consists of a VH domain; and (vi) an isolated complementarity determining region (CDR). Single chain antibodies are also intended to be encompassed within the term "antigen-binding portion" of an antibody. These antibody fragments are obtained using conventional techniques known to those with skill in the art, and the fragments are screened for utility in the same manner as are intact antibodies.

The terms "monoclonal antibody" or "monoclonal antibody composition" as used herein refer to a preparation of antibody molecules of single molecular composition. A monoclonal antibody composition displays a single binding specificity and affinity for a particular epitope.

The term "human antibody", as used herein, is intended to include antibodies having variable regions in which both the framework and CDR regions are derived from human germline immunoglobulin sequences.

The term "humanized antibody" is intended to refer to antibodies in which CDR sequences derived from the germline of another mammalian species, such as a mouse, have been grafted onto human framework sequences. Additional framework region modifications may be made within the human framework sequences.

In addition to antibodies, other biological molecules may act as checkpoint inhibitors, including peptides having binding affinity to the appropriate target.

The term "treatment" or "therapy" refers to administering an active agent with the purpose to cure, heal, alleviate, relieve, alter, remedy, ameliorate, improve, or affect a condition (e.g., a disease), the symptoms of the condition, or to prevent or delay the onset of the symptoms, complications, biochemical indicia of a disease, or otherwise arrest or inhibit further development of the disease, condition, or disorder in a statistically significant manner.

As used herein, the term "subject" is intended to include human and non-human animals. Preferred subjects include human patients in need of enhancement of an immune response. The methods are particularly suitable for treating human patients having a disorder that can be treated by augmenting the T-cell mediated immune response. In a particular embodiment, the methods are particularly suitable for treatment of cancer cells in vivo.

As used herein, the terms "concurrent administration" or "concurrently" or "simultaneous" mean that administration occurs on the same day. The terms "sequential administration" or "sequentially" or "separate" mean that administration occurs on different days.

"Simultaneous" administration, as defined herein, includes the administration of the immunomodulator and agent or procedure comprising checkpoint inhibitor therapy within about 2 hours or about 1 hour or less of each other, even more preferably at the same time.

"Separate" administration, as defined herein, includes the administration of the immunomodulator and agent or procedure comprising checkpoint inhibitor therapy, more than about 12 hours, or about 8 hours, or about 6 hours or about 4 hours or about 2 hours apart.

"Sequential" administration, as defined herein, includes the administration of the immunomodulator and chemotherapeutic agent each in multiple aliquots and/or doses and/or on separate occasions. The immunomodulator may be administered to the patient after before and/or after administration of the checkpoint inhibitor. Alternatively, the immunomodulator is continued to be applied to the patient after treatment with a checkpoint inhibitor.

The use of the alternative (e.g., "or") should be understood to mean either one, both, or any combination thereof of the alternatives. As used herein, the indefinite articles "a" or "an" should be understood to refer to "one or more" of any recited or enumerated component.

As used herein, "about" means within an acceptable error range for the particular value as determined by one of ordinary skill in the art, which will depend in part on how the value is measured or determined, i.e., the limitations of the measurement system. For example, "about" can mean within 1 or more than 1 standard deviation per the practice in the art. Alternatively, "about" can mean a range of up to 20%. When particular values are provided in the application and claims, unless otherwise stated, the meaning of "about" should be assumed to be within an acceptable error range for that particular value.

In one aspect of the present invention the immunomodulator comprises a whole cell, non-pathogenic heat-killed *Mycobacterium*. Examples of mycobacterial species for use in the present invention include *M. vaccae, M. thermoresistibile, M. flavescens, M. duvalii, M. phlei, M. obuense, M. parafortuitum, M. sphagni, M. aichiense, M. rhodesiae, M. neoaurum, M. chubuense, M. tokaiense, M. komossense, M. aurum, M. w, M. tuberculosis, M. microti; M. africanum; M. kansasii, M. marinum; M. simiae; M. gastri; M. nonchromogenicum; M. terrae; M. triviale; M. gordonae; M. scrofulaceum; M. paraffinicum; M. intracellulare; M. avium; M. xenopi; M. ulcerans; M. diernhoferi, M. smegmatis; M. thamnopheos; M. flavescens; M. fortuitum; M. peregrinum; M. chelonei; M. paratuberculosis; M. leprae; M. lepraemurium* and combinations thereof.

The whole cell non-pathogenic heat-killed *Mycobacterium* is preferably selected from *M. vaccae, M. obuense, M. parafortuitum, M. aurum, M. indicus pranii, M. phlei* and combinations thereof. More preferably the whole cell, non-pathogenic heat-killed *Mycobacterium* is a rough variant. The amount of *Mycobacterium* administered to the patient is sufficient to elicit a protective immune response in the patient such that the patient's immune system is able to mount an effective immune response to the cancer or tumour. In certain embodiments of the invention, there is provided a containment means comprising the effective amount of heat-killed *Mycobacterium* for use in the present invention, which typically may be from $10^3$ to $10^{11}$ organisms, preferably from $10^4$ to $10^{10}$ organisms, more preferably from $10^6$ to $10^{10}$ organisms, and even more preferably from $10^6$ to $10^9$ organisms. The effective amount of heat-killed *Mycobacterium* for use in the present invention may be from $10^3$ to $10^{11}$ organisms, preferably from $10^4$ to $10^{10}$ organisms, more preferably from $10^6$ to $10^{10}$ organisms, and even more preferably from $10^6$ to $10^9$ organisms. Most preferably the amount of heat-killed *Mycobacterium* for use in the present invention is from $10^7$ to $10^9$ cells or organisms. Typically, the composition according to the present invention may be administered at a dose of from $10^8$ to $10^9$ cells for human and animal use. Alternatively the dose is from 0.01 mg to 1 mg or 0.1 mg to 1 mg organisms presented as either a suspension or dry preparation.

*M. vaccae* and *M. obuense* are particularly preferred.

*M. vaccae* and *M. obuense* induce a complex immune response in the host. Treatment with these preparations will stimulate innate and type-1 immunity, including Th1 and macrophage activation and cytotoxic cell activity. They also independently down-regulate inappropriate Th2 responses via immunoregulatory mechanisms. This restores the healthy balance of the immune system.

The present invention may be used to treat a neoplastic disease, such as solid or non-solid cancers. As used herein, "treatment" encompasses the prevention, reduction, control and/or inhibition of a neoplastic disease. Such diseases include a sarcoma, carcinoma, adenocarcinoma, melanoma, myeloma, blastoma, glioma, lymphoma or leukemia. Exemplary cancers include, for example, carcinoma, sarcoma, adenocarcinoma, melanoma, neural (blastoma, glioma), mesothelioma and reticuloendothelial, lymphatic or haematopoietic neoplastic disorders (e.g., myeloma, lymphoma or leukemia). In particular aspects, a neoplasm, tumour or cancer includes a lung adenocarcinoma, lung carcinoma, diffuse or interstitial gastric carcinoma, colon adenocarcinoma, prostate adenocarcinoma, esophagus carcinoma, breast carcinoma, pancreas adenocarcinoma, ovarian adenocarcinoma, adenocarcinoma of the adrenal gland, adenocarcinoma of the endometrium or uterine adenocarcinoma.

Neoplasia, tumours and cancers include benign, malignant, metastatic and non-metastatic types, and include any stage (I, II, III, IV or V) or grade (G1, G2, G3, etc.) of neoplasia, tumour, or cancer, or a neoplasia, tumour, cancer or metastasis that is progressing, worsening, stabilized or in remission. Cancers that may be treated according to the invention include but are not limited to: bladder, blood, bone, bone marrow, brain, breast, colon, esophagus, gastrointestines, gum, head, kidney, liver, lung, nasopharynx, neck, ovary, prostate, skin, stomach, testis, tongue, or uterus. Preferably, the cancer is selected from prostate cancer, liver cancer, renal cancer, lung cancer, breast cancer, colorectal cancer, pancreatic cancer, brain cancer, hepatocellular cancer, lymphoma, leukaemia, gastric cancer, cervical cancer, ovarian cancer, thyroid cancer, melanoma, head and neck cancer, skin cancer and soft tissue sarcoma and/or other forms of carcinoma. The tumour may be metastatic or a malignant tumour.

More preferably, the cancer is pancreatic, colorectal, prostate, ovarian or prostate cancer a.

In an embodiment of the invention, the checkpoint inhibitor therapy comprising administration of a blocking agent, selected from a cell, protein, peptide, antibody or antigen binding fragment thereof, directed against CTLA-4, PD-1, PD-L1, PD-L2, LAG-3, B7-H3, B7-H4, B7-H6, A2AR, or IDO, and combinations thereof, in combination with a whole cell, non-pathogenic heat-killed *Mycobacterium*, is used to reduce or inhibit metastasis of a primary tumour or cancer to other sites, or the formation or establishment of metastatic tumours or cancers at other sites distal from the primary tumour or cancer thereby inhibiting or reducing tumour or cancer relapse or tumour or cancer progression. Preferably, the blocking agent is directed against CTLA-4, PD-1, or PD-L1, and combinations thereof. Most preferably, the blocking agent is directed against PD-L1.

In a further embodiment of the invention, there is provided a combination therapy for treating cancer, comprising an immunomodulator and checkpoint inhibitor(s), wherein said checkpoint inhibition therapy comprises administration of a blocking agent, selected from a cell, protein, peptide, antibody or antigen binding fragment thereof, directed against CTLA-4, PD-1, PD-L1, PD-L2, LAG-3, B7-H3, B7-H4, B7-H6, A2AR, or IDO, and combinations thereof, wherein the immunomodulator comprises a whole cell, non-pathogenic heat-killed *Mycobacterium*, with the potential to elicit potent and durable immune responses with enhanced therapeutic benefit and more manageable toxicity. Preferably, the blocking agent is directed against CTLA-4, PD-1, or PD-L1, and combinations thereof. Most preferably, the blocking agent is directed against PD-L1.

In a further embodiment of the invention, there is provided a combination therapy for treating cancer, comprising an immunomodulator which; (i) stimulates innate and type-1 immunity, including Th1 and macrophage activation and cytotoxic cell activity, and, (ii) independently down-regulates inappropriate Th2 responses via immunoregulatory mechanisms; and, a checkpoint inhibitor, optionally wherein the immunomodulator is a whole cell non-pathogenic, heat-killed *Mycobacterium* selected from *M. vaccae* or *M. obuense*.

In an embodiment of the invention is provided a method for treating cancer and/or preventing the establishment of metastases by employing a checkpoint inhibitor selected from a cell, protein, peptide, antibody or antigen binding fragment thereof, directed against CTLA-4, PD-1, PD-L1, PD-L2, LAG-3, B7-H3, B7-H4, B7-H6, A2AR, or IDO, and combinations thereof, which act synergistically with a whole cell non-pathogenic, heat-killed *Mycobacterium*. Preferably, the checkpoint inhibitor employed is directed against CTLA-4, PD-1, or PD-L1, and combinations thereof. Most preferably, the blocking agent is directed against PD-L1.

In further embodiments, methods of the invention include, one or more of the following: 1) reducing or inhibiting growth, proliferation, mobility or invasiveness of tumour or cancer cells that potentially or do develop metastases, 2) reducing or inhibiting formation or establishment of metastases arising from a primary tumour or cancer to one or more other sites, locations or regions distinct from the primary tumour or cancer; 3) reducing or inhibiting growth or proliferation of a metastasis at one or more other sites, locations or regions distinct from the primary tumour or cancer after a metastasis has formed or has been established, 4) reducing or inhibiting formation or establishment of additional metastasis after the metastasis has been formed or established, 5) prolonged overall survival, 6) prolonged progression free survival, or 7) disease stabilisation.

In an embodiment of the invention, administration of the checkpoint inhibitor, selected from a cell, protein, peptide, antibody or antigen binding fragment thereof, directed against CTLA-4, PD-1, PD-L1, PD-L2, LAG-3, B7-H3, B7-H4, B7-H6, A2AR, or IDO, and combinations thereof, in combination therapy with a whole cell, heat-killed non-pathogenic *Mycobacterium*, provides a detectable or measurable improvement in a condition of a given subject, such as alleviating or ameliorating one or more adverse (physical) symptoms or consequences associated with the presence of a cell proliferative or cellular hyperproliferative disorder, neoplasia, tumour or cancer, or metastasis, i e., a therapeutic benefit or a beneficial effect.

Preferably, the blocking agent is directed against CTLA-4, PD-1, or PD-L1, and combinations thereof. Most preferably, the blocking agent is directed against PD-L1.

A therapeutic benefit or beneficial effect is any objective or subjective, transient, temporary, or long-term improvement in the condition or pathology, or a reduction in onset, severity, duration or frequency of an adverse symptom associated with or caused by cell proliferation or a cellular hyperproliferative disorder such as a neoplasia, tumour or cancer, or metastasis. It may lead to improved survival. A satisfactory clinical endpoint of a treatment method in accordance with the invention is achieved, for example, when there is an incremental or a partial reduction in severity, duration or frequency of one or more associated pathologies, adverse symptoms or complications, or inhibition or reversal of one or more of the physiological, biochemical or cellular manifestations or characteristics of cell proliferation or a cellular hyperproliferative disorder such as a neoplasia, tumour or cancer, or metastasis. A therapeutic benefit or improvement therefore may be, but is not limited to destruction of target proliferating cells (e.g., neoplasia, tumour or cancer, or metastasis) or ablation of one or more, most or all pathologies, adverse symptoms or complications associated with or caused by cell proliferation or the cellular hyperproliferative disorder such as a neoplasia, tumour or cancer, or metastasis. However, a therapeutic benefit or improvement need not be a cure or complete destruction of all target proliferating cells (e.g., neoplasia, tumour or cancer, or metastasis) or ablation of all pathologies, adverse symptoms or complications associated with or caused by cell proliferation or the cellular hyperproliferative disorder such as a neoplasia, tumour or cancer, or metastasis. For example, partial destruction of a tumour or cancer cell mass, or a stabilization of the tumour or cancer mass, size or cell numbers by inhibiting progression or worsening of the tumour or cancer, can reduce mortality and prolong lifespan even if only for a few days, weeks or months, even though a portion or the bulk of the tumour or cancer mass, size or cells remain.

Specific non-limiting examples of therapeutic benefit include a reduction in neoplasia, tumour or cancer, or metastasis volume (size or cell mass) or numbers of cells, inhibiting or preventing an increase in neoplasia, tumour or cancer volume (e.g., stabilizing), slowing or inhibiting neoplasia, tumour or cancer progression, worsening or metastasis, or inhibiting neoplasia, tumour or cancer proliferation, growth or metastasis.

In an embodiment of the invention, administration of the checkpoint inhibitor, selected from a cell, protein, peptide, antibody or antigen binding fragment thereof, directed against CTLA-4, PD-1, PD-L1, PD-L2, LAG-3, B7-H3, B7-H4, B7-H6, A2AR, or IDO, and combinations thereof, in combination therapy with the whole cell, non-pathogenic heat-killed *Mycobacterium*, provides a detectable or measurable improvement or overall response according to the irRC (as derived from time-point response assessments and based on tumour burden), including one of more of the following: (i) irCR—complete disappearance of all lesions, whether measurable or not, and no new lesions (confirmation by a repeat, consecutive assessment no less than 4 weeks from the date first documented), (ii) irPR—decrease in tumour burden 50% relative to baseline (confirmed by a consecutive assessment at least 4 weeks after first documentation). Preferably, the checkpoint inhibitor employed is directed against CTLA-4, PD-1, or PD-L1, and combinations thereof.

An invention method may not take effect immediately. For example, treatment may be followed by an increase in the neoplasia, tumour or cancer cell numbers or mass, but over time eventual stabilization or reduction in tumour cell mass, size or numbers of cells in a given subject may subsequently occur.

Additional adverse symptoms and complications associated with neoplasia, tumour, cancer and metastasis that can be inhibited, reduced, decreased, delayed or prevented include, for example, nausea, lack of appetite, lethargy, pain and discomfort. Thus, a partial or complete decrease or reduction in the severity, duration or frequency of an adverse symptom or complication associated with or caused by a cellular hyperproliferative disorder, an improvement in the subjects quality of life and/or well-being, such as increased energy, appetite, psychological well-being, are all particular non-limiting examples of therapeutic benefit.

A therapeutic benefit or improvement therefore can also include a subjective improvement in the quality of life of a treated subject. In an additional embodiment, a method prolongs or extends lifespan (survival) of the subject. In a further embodiment, a method improves the quality of life of the subject.

In a most preferred embodiment, administration of the checkpoint inhibitor, selected from a cell, protein, peptide, antibody or antigen binding fragment thereof, directed against CTLA-4, PD-1, PD-L1, PD-L2, LAG-3, B7-H3, B7-H4, B7-H6, A2AR, or IDO, and combinations thereof, in combination therapy with a whole cell, non-pathogenic heat-killed *Mycobacterium* results in a clinically relevant improvement in one or more markers of disease status and progression selected from one or more of the following: (i): overall survival, (ii): progression-free survival, (iii): overall response rate, (iv): reduction in metastatic disease, (v): circulating levels of tumour antigens such as carbohydrate antigen 19.9 (CA19.9) and carcinembryonic antigen (CEA) or others depending on tumour, (vii) nutritional status (weight, appetite, serum albumin), (viii): pain control or analgesic use, (ix): CRP/albumin ratio. Preferably, the checkpoint inhibitor adminstered is directed against CTLA-4, PD-1, or PD-L1, and combinations thereof.

Treatment with non-pathogenic, heat-killed whole cell *M. vaccae* and *M. obuense* gives rise to more complex immunity including not only the development of innate immunity and type-1 immunity, but also immunoregulation which more efficiently restores appropriate immune functions.

In another preferred embodiment, the checkpoint inhibition therapy comprises administration of a sub-therapeutic amount and/or duration of a blocking agent, selected from a cell, protein, peptide, antibody or antigen binding fragment thereof, directed against CTLA-4, PD-1, PD-L1, PD-L2, LAG-3, B7-H3, B7-H4, B7-H6, A2AR, or IDO, and combinations thereof. Preferably, the checkpoint inhibition therapy comprises administration of a sub-therapeutic amount of a blocking agent directed against CTLA-4, PD-1, or PD-L1, and combinations thereof.

In a further preferred embodiment, the checkpoint inhibition therapy comprises administration of a blocking agent, selected from a cell, protein, peptide, antibody or antigen binding fragment thereof, directed against PD-1 and/or, PD-L1.

In a further preferred embodiment, the checkpoint inhibition therapy comprises administration of a blocking agent, selected from a cell, protein, peptide, antibody or antigen binding fragment thereof, directed against PD-1 and/or, PD-L1, simultaneously, separately or sequentially with administration of a blocking antibody or antigen binding fragment thereof, directed against CTLA-4.

In a further preferred embodiment, the checkpoint inhibition therapy comprises administration of a blocking agent, wherein said blocking agent is an antibody selected from the group consisting of: ipilimumab, nivolumab, pembrolizumab, atezolizumab, tremelimumab (as described in WO2006/101692), MED1-0680 (Astra Zeneca), MDX-1105 (Medarex), MED1-4736 (Medimmune, Inc.) or MSB001078C (Merck KGaA), and combinations thereof.

In a further preferred embodiment, the checkpoint inhibition therapy comprises administration of a blocking agent, wherein said blocking agent is an antibody selected from ipilimumab, nivolumab, pembrolizumab, atezolizumab, tremelimumab, and combinations thereof.

In a further preferred embodiment, the checkpoint inhibition therapy comprises administration of a blocking agent wherein said blocking agent is pembrolizumab (as described in WO2012/135408), and wherein said patient has mismatch-repair deficient tumours associated with said cancer and/or exhibits PD-L1 expression in at least 10%, or 20%, or 30%, or 40%, or 50% or more of tumour cells, as measured using the SP142 immunohistochemistry antibody assay In a further preferred embodiment, the checkpoint inhibition therapy comprises administration of a blocking agent, wherein said blocking agent is ipilimumab (as described in U.S. Pat. Nos. 9,868,388, 8,962,804 and 8,809,562) and administered intravenously at a dose of 2 mg/mg or less every three weeks, optionally for a maximum of four infusions.

In a further preferred embodiment, the checkpoint inhibition therapy comprises administration of a blocking agent, wherein said blocking agent is nivolumab (Humab ref: 5C4 as described in U.S. Pat. No. 8,004,449) and administered intravenously at a dose of at least 3, or 5 or 10 mg/mg or more every four weeks, optionally wherein said patient exhibits PD-L1 expression in at least 1%, 5% or 10% or more of tumour cells, as measured using the SP142 immunohistochemistry antibody assay.

In a further preferred embodiment, the checkpoint inhibition therapy comprises administration of a blocking agent wherein said blocking agent is atezolizumab (sequence 21 from US 8217149) and administered intravenously at a dose of at least 10 or 15 mg/kg or more every three weeks, optionally wherein said patient exhibits PD-L1 expression in at least 1%, 5% or 10% or more of tumour cells and/or tumour-infiltrating immune cells selected from B-cells and NK cells, as measured using the SP142 immunohistochemistry antibody assay.

In another preferred embodiment, the checkpoint inhibition therapy comprises administration of a blocking agent, selected from a cell, protein, peptide, antibody or antigen binding fragment thereof, directed against PD-L2.

In a further preferred embodiment, the checkpoint inhibition therapy comprises administration of a blocking agent, selected from a cell, protein, peptide, antibody or antigen binding fragment thereof, directed against, PD-L2, simultaneously, separately or sequentially with administration of a blocking antibody or antigen binding fragment thereof, directed against CTLA-4.

In a further preferred embodiment, the checkpoint inhibition therapy comprises administration of a blocking agent, wherein said blocking agent is an antibody selected from the group consisting of: AMP-224 (Amplimmune, Inc), BMS-986016 or MGA-271, and combinations thereof.

AMP-224, also known as B7-DCIg, is a PD-L2-Fc fusion soluble receptor described in WO2010/027827 and WO2011/066342.

BMS-986016 is a fully human antibody specific for human LAG-3 that was isolated from immunized transgenic mice expressing human immunoglobulin genes. It is expressed as an IgG4 isotype antibody that includes a stabilizing hinge mutation (S228P) for attenuated Fc receptor binding in order to reduce or eliminate the possibility of antibody- or complement-mediated target cell killing. The heavy and light chain amino acid sequences of BMS-986016 are provided in SEQ ID NOs: 17 and 18 of WO2015/042246.

In another embodiment, the checkpoint inhibition therapy comprises administration of BMS-986016 administered intravenously at a dose of between about 20 mg and about 8000 mg, every two weeks, optionally for a maximum of forty eight infusions.

In a further embodiment, the checkpoint inhibition therapy comprises administration of a blocking agent wherein said blocking agent is an antibody that specifically binds to B7-H3 such as MGA271 (an a-B7-H3 humanized monoclonal antibody; Macrogenics, Inc.) or other antibodies as described in US Application Publication Number 2012-0294796, the contents of which are incorporated herein by reference; or indoleamine-2,3-dioxygenase (IDO) inhibitors such as D-l-methyl-tryptophan (Lunate) and other compounds described in U.S. Pat. No. 7,799,776, the contents of which are incorporated herein by reference The term "combination" as used throughout the specification, is meant to encompass the administration of the checkpoint inhibitor simultaneously, separately or sequentially with administration of the whole cell, non-pathogenic heat-killed *Mycobacterium*. Accordingly, the checkpoint inhibitor and the whole cell, non-pathogenic heat-killed *Mycobacterium* may be present in the same or separate pharmaceutical formulations, and administered at the same time or at different times.

Thus, a whole cell, non-pathogenic heat-killed *Mycobacterium* and the checkpoint inhibitor may be provided as separate medicaments for administration at the same time or at different times.

Preferably, a whole cell, non-pathogenic heat-killed *Mycobacterium* and checkpoint inhibitor are provided as separate medicaments for administration at different times. When administered separately and at different times, either the whole cell, non-pathogenic heat-killed *Mycobacterium* or checkpoint inhibitor may be administered first; however, it is suitable to administer checkpoint inhibitor followed by the whole cell, non-pathogenic heat-killed *Mycobacterium*. In addition, both can be administered on the same day or at different days, and they can be administered using the same schedule or at different schedules during the treatment cycle.

In an embodiment of the invention, a treatment cycle consists of the administration of a whole cell, non-pathogenic heat-killed *Mycobacterium* daily, weekly fortnightly or monthly, simultaneously with checkpoint inhibitor weekly. Alternatively, the whole cell, non-pathogenic heat-killed *Mycobacterium* is administered before and/or after the administration of the checkpoint inhibitor.

In another embodiment of the invention, the whole cell, non-pathogenic heat-killed *Mycobacterium* is administered to the patient before and after administration of a checkpoint inhibitor. That is, in one embodiment, the whole cell, non-pathogenic heat-killed *Mycobacterium* is administered to the patient before and after said checkpoint inhibitor.

Dose delays and/or dose reductions and schedule adjustments are performed as needed depending on individual patient tolerance to treatments.

Alternatively, the administration of checkpoint inhibitor may be performed simultaneously with the administration of the effective amounts of the whole cell, non-pathogenic heat-killed *Mycobacterium*.

The whole cell, non-pathogenic heat-killed *Mycobacterium*, may be administered to the patient via the parenteral, oral, sublingual, nasal or pulmonary route. In a preferred embodiment, the immunomodulator is administered via a parenteral route selected from subcutaneous, intradermal, subdermal, intraperitoneal, intravenous and intravesicular injection. Alternatively, administration by the parenteral route may comprise intratumoural injection of said non-pathogenic heat-killed *Mycobacterium* and/or blocking agent The subject whom is to undergo checkpoint inhibition therapy according to the present invention may do so simultaneously, separately or sequentially with administration of the whole cell, non-pathogenic heat-killed *Mycobacterium*.

In an aspect of the invention, the effective amount of the whole cell, non-pathogenic heat-killed *Mycobacterium* may be administered as a single dose. Alternatively, the effective amount of the whole cell, non-pathogenic heat-killed *Mycobacterium* may be administered in multiple (repeat) doses, for example two or more, three or more, four or more, five or more, ten or more, or twenty or more repeat doses. The whole cell non-pathogenic heat-killed *Mycobacterium* may be administered between about 4 weeks and about 1 day prior to checkpoint inhibition therapy, such as between about 4 weeks and 1 week, or about between 3 weeks and 1 week, or about between 3 weeks and 2 weeks. Administration may be presented in single or multiple doses.

In a preferred embodiment of the invention there is a whole cell, non-pathogenic heat-killed *Mycobacterium*. for use in the treatment of neoplastic disease in combination with a checkpoint inhibitor, selected from a cell, protein, peptide, antibody or antigen binding fragment thereof, directed against CTLA-4, PD-1, PD-L1, PD-L2, LAG-3, B7-H3, B7-H4, B7-H6, A2AR, or IDO, and combinations thereof, wherein said *Mycobacterium* is administered to the subject before, concurrently with and/or after the checkpoint inhibitor is administered. Preferably, the *Mycobacterium* is for use in treatment of a neoplastic disease in combination with checkpoint inhibitors directed against PD-1, PD-L1, or CTLA-4, and combinations thereof.

In another preferred embodiment of the invention is a method of treating, reducing, inhibiting or controlling a neoplasia, tumour or cancer in a subject, wherein said method comprises simultaneously, separately or sequentially administering to the subject, (i) a checkpoint inhibitor, selected from a cell, protein, peptide, antibody or antigen binding fragment thereof, directed against CTLA-4, PD-1, PD-L1, PD-L2, LAG-3, B7-H3, B7-H4, B7-H6, A2AR, or IDO, and combinations thereof, and (ii) an immunomodulator, wherein said method results in enhanced therapeutic efficacy relative to administration of the checkpoint inhibitor or immunomodulator alone, and wherein the immunomodulator comprises a whole cell, non-pathogenic heat-killed *Mycobacterium*, and optionally wherein said method comprises administration of a sub-therapeutic amount of said checkpoint inhibitor.

Preferably, the checkpoint inhibitor is directed against CTLA-4, PD-1, or PD-L1, and combinations thereof. Most preferably, the blocking agent is directed against PD-L1.

In another preferred embodiment of the invention is a method of treating, reducing, inhibiting or controlling a neoplasia, tumour or cancer in a subject, wherein said method comprises simultaneously, separately or sequentially administering to the subject, (i) a checkpoint inhibitor, and (ii) an immunomodulator, preferably a whole cell heat-killed *Mycobacterium*, wherein said checkpoint inhibition therapy comprises administration of a blocking agent, selected from a cell, protein, peptide, antibody or antigen binding fragment thereof, directed against PD-1 and/or PD-L1.

In yet another preferred embodiment of the invention is a method of treating, reducing, inhibiting or controlling a neoplasia, tumour or cancer in a subject, wherein said method comprises simultaneously, separately or sequentially administering to the subject, (i) a checkpoint inhibitor, and (ii) a whole cell, non-pathogenic heat-killed *Mycobacterium*, wherein said checkpoint inhibition therapy comprises administration of a blocking agent, selected from an antibody or antigen binding fragment thereof, directed against CTLA-4, PD-1 or PD-L1, and combinations thereof, wherein said checkpoint inhibition therapy comprises administration of a sub-therapeutic amount and/or duration of said blocking antibody or antigen binding fragment thereof.

In yet another embodiment of the invention is a method of treating, reducing, inhibiting or controlling a neoplasia, tumour or cancer in a subject, wherein said method comprises simultaneously, separately or sequentially administering to the subject, (i) two or more checkpoint inhibitors, and (ii) a whole cell, non-pathogenic heat-killed *Mycobacterium*, wherein said checkpoint inhibition therapy comprises administration of two or more blocking agent, selected from a cell, protein, peptide, antibody or antigen binding fragment thereof, directed against CTLA-4, PD-1 or PD-L1, and combinations thereof, wherein said checkpoint inhibition therapy optionally comprises administration of a sub-therapeutic amount and/or duration of either blocking agent.

In one embodiment of the present invention, the whole cell, non-pathogenic heat-killed *Mycobacterium* may be in the form of a medicament administered to the patient in a dosage form.

A container according to the invention in certain instances may be a vial, an ampoule, a syringe, capsule, tablet or a tube. In some cases, the mycobacteria may be lyophilized and formulated for resuspension prior to administration. However, in other cases, the mycobacteria are suspended in a volume of a pharmaceutically acceptable liquid. In some of the most preferred embodiments there is provided a container comprising a single unit dose of mycobacteria suspended in pharmaceutically acceptable carrier wherein the unit dose comprises about $1 \times 10^6$ to about $1 \times 10^{10}$ organisms. In some very specific embodiments the liquid comprising suspended mycobacteria is provided in a volume of between about 0.1 ml and 10 ml, or between about 0.3 ml and 2 ml or between about 0.5 ml and 2 ml. The foregoing compositions provide ideal units for immunotherapeutic applications described herein.

Embodiments discussed in the context of a methods and/or composition of the invention may be employed with respect to any other method or composition described herein. Thus, an embodiment pertaining to one method or composition may be applied to other methods and compositions of the invention as well.

In some cases, whole cell non-pathogenic heat-killed Mycobacteria are administered to specific sites on or in a subject. For example, the mycobacterial compositions according to the invention, such as those comprising *M. obuense* in particular, may be administered adjacent to tumours or adjacent to lymph nodes, such as those that drain tissue surrounding a tumour. Thus, in certain instances sites administration of mycobacterial composition may be near the posterior cervical, tonsillar, axillary, inguinal, anterior cervical, sub-mandibular, sub mental or superclavicular lymph nodes.

The whole cell, non-pathogenic heat-killed *Mycobacterium* may be administered for the length of time the cancer or tumour(s) is present in a patient or until such time the cancer has regressed or stabilized. The whole cell, non-pathogenic heat-killed *Mycobacterium* r may also be continued to be administered to the patients once the cancer or tumour has regressed or stabilised.

Mycobacterial compositions according to the invention will comprise an effective amount of mycobacteria typically dispersed in a pharmaceutically acceptable carrier. The phrases "pharmaceutically or pharmacologically acceptable" refers to molecular entities and compositions that do not produce an adverse, allergic or other untoward reaction when administered to an animal, such as, for example, a human, as appropriate. The preparation of an pharmaceutical composition that contains mycobacteria will be known to those of skill in the art in light of the present disclosure, as exemplified by Remington's Pharmaceutical Sciences, 18th Ed. Mack Printing Company, 1990, Moreover, for animal (e.g., human) administration, it will be understood that preparations should meet sterility, pyrogenicity, general safety and purity standards. A specific example of a pharmacologically acceptable carrier as described herein is borate buffer or sterile saline solution (0.9% NaCl).

As used herein, "pharmaceutically acceptable carrier" includes any and all solvents, dispersion media, coatings, surfactants, antioxidants, preservatives {e.g., antibacterial agents, antifungal agents), isotonic agents, absorption delaying agents, salts, preservatives, drugs, drug stabilizers, gels, binders, excipients, disintegration agents, lubricants, sweetening agents, flavouring agents, dyes, such like materials and combinations thereof, as would be known to one of ordinary skill in the art (see, for example, Remington's Pharmaceutical Sciences, 18th Ed. Mack Printing Company, 1990, pp. 1289-1329).

In a preferred embodiment, the whole cell, non-pathogenic heat-killed *Mycobacterium* is administered via a parenteral route selected from subcutaneous, intradermal, subdermal, intraperitoneal, intravenous and intravesicular injection. Intradermal injection enables delivery of an entire proportion of the mycobacterial composition to a layer of the dermis that is accessible to immune surveillance and thus capable of electing an anti-cancer immune response and promoting immune cell proliferation at local lymph nodes.

Though in highly preferred embodiments of the invention mycobacterial compositions are administered by direct intradermal injection, it is also contemplated that other methods of administration may be used in some case. Thus in certain instances, the whole cell, non-pathogenic heat-killed *Mycobacterium* of the present invention can be administered by injection, infusion, continuous infusion, intravenously, intradermally, intraarterially, intraperitoneally, intralesionally, intravitreally, intravaginally, intrarectally, topically, intratumourally, intramuscularly, intraperitoneally, subcutaneously, subconjunctival, intravesicularlly, mucosally, intrapericardially, intraumbilically, intraocularally, orally, intracranially, intraarticularly, intraprostaticaly, intrapleurally, intratracheally, intranasally, topically, locally, inhalation (e.g. aerosol inhalation), via a catheter, via a lavage, or by other method or any combination of the forgoing as would be known to one of ordinary skill in the art (see, for example, Remington's Pharmaceutical Sciences, 18th Ed. Mack Printing Company, 1990).

All publications mentioned in the above specification are herein incorporated by reference. Various modifications and variations of the described methods and system of the present invention will be apparent to those skilled in the art without departing from the scope and spirit of the present invention. Although the present invention has been described in connection with specific preferred embodiments, it should be understood that the invention as claimed should not be unduly limited to such specific embodiments. Indeed, various modifications of the described modes for carrying out the invention which are obvious to those skilled in biochemistry and immunology or related fields are intended to be within the scope of the following claims.

The invention is further described with reference to the following non-limiting Example.

Example 1

Adult C57BL/6 mice were injected subcutaneously on the flank with $10^5$ cells from a pancreatic cancer cell line obtained from KPC mice (Hingorani et al. Cancer Cell, 2005, 7:469-48). These murine pancreatic cancer cells bear mutations in Kras, p53 and Pdx-Cre (Hingorani et al. Cancer Cell, 2005, 7:469-48).

When the injected tumour cells had grown to become a palpable tumour (day 0), mice were left untreated or received treatment with:
1) 0.1 mg *M. obuense* NTCT 13365/mouse, subcutaneously alternating injections in the scruff of the neck with those at the base of the tail on alternating days over 5 day period with a 2 day break for the length of the study;
2) 10 mg/kg anti-PDL-1 mAb or 10 mg/kg anti PD-1 mAb intraperitoneally once weekly;
3) the combination of anti-PDL-1 or 10 mg/kg anti PD-1 mAb and *M. obuense* NTCT 13365 at a dose and schedule described above for the two compounds used singly.

Tumour growth was monitored over the course of the study to determine whether the treatment administered had an effect on reducing tumour size and improving prospects of survival.

Figure 1:
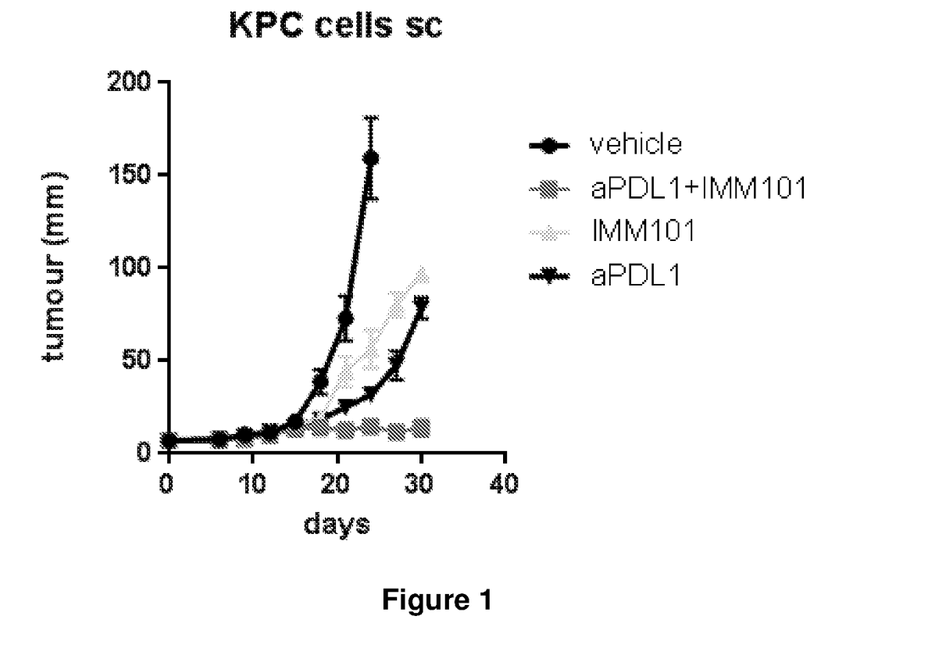
FIG. 1 shows the effect of a preparation of heat-killed *Mycobacterium obuense* (NCTC 13365) with or without co-administration of a checkpoint inhibitor (ant-PD-L1 mAb), in a xenograft model of pancreatic cancer (KPC cells injected subcutaneously).
Figure 2:
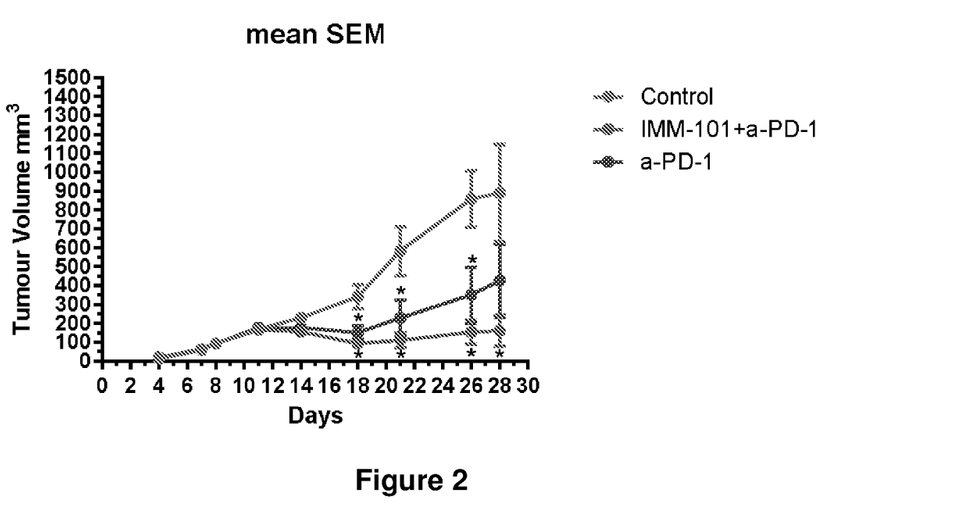
FIG. 2—is as above except that the co-administered checkpoint inhibitor is an anti-PD-1 mAb.

Data presented in FIG. 1 show that mice which received the treatment combination of anti-PDL-1 and *M. obuense* NTCT 13365 demonstrated a continued reduction in tumour size and appeared to control the tumour. This reduction in tumour size was more pronounced compared to mice receiving either treatment alone. Mice left untreated had uncontrolled tumour growth and soon succumbed to the disease.

Example 2

The effects of combination treatment with IMM-101 and checkpoint inhibitors were investigated in C57BL/6 mice bearing subcutaneous B16-F10 tumours.

Figure 3:
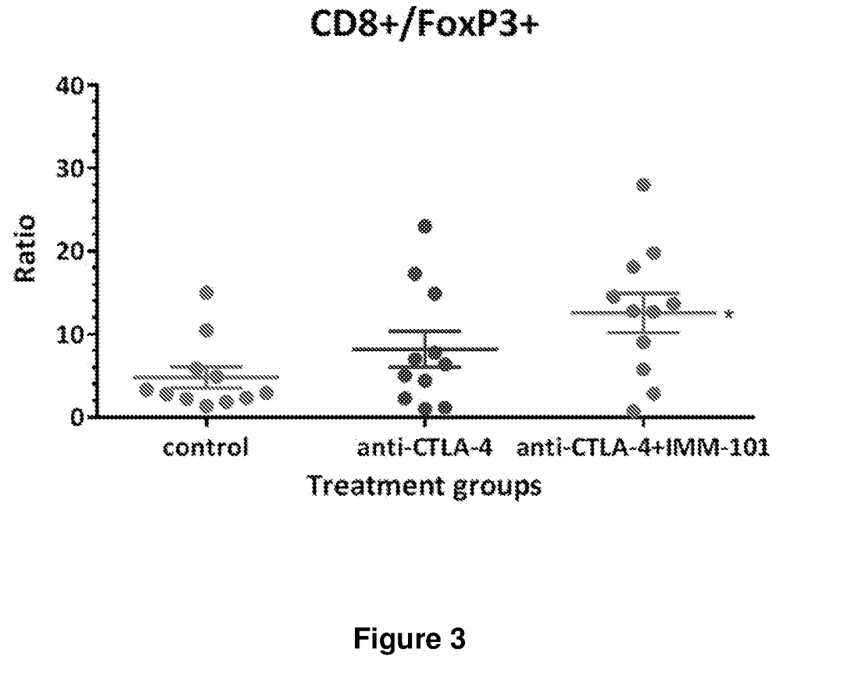
FIG. 3 shows the ratio of CD3+CD8+ cells and FoxP3 Treg cells infiltrating the tumours in control mice (red), mice that have received anti-CTLA-4 treatment only (blue) or mice that have received combination treatment consisting of IMM-101 and anti-CTLA-4 (green). We found a significant increase (Anova $p<0.05$) in this group.

The mice were engrafted at D0. Mice were randomized on D1 and received a total of 8 SC injections of IMM-101 at 0.1 mg/mouse on D1, D3, D5, D7, D9, D11, D13 and D15 (half of surviving mice) or D16 (half of surviving mice) (Q2D×8) or a total of 4 IP injections of anti-PD1 or anti-CTLA4 at 10 mg/kg (twice weekly for two consecutive weeks on D1, D5, D8 and D12: TW×2) alone or in combination. At Day 15 and 16, half of all surviving mice were terminated after the last treatment. The tumour immune infiltrate cells and spleen immune cells (the ratio of CD3+CD8+ cells and FoxP3 Treg cells) characterization were quantified by FACS analysis (FIG. 3).

We claim:
1. A method of treating, reducing, inhibiting or controlling a neoplasia, tumour or cancer in a subject, wherein said method comprises administering to the subject, (i) a checkpoint inhibitor comprising a human or humanized antibody directed against PD-L1, a human or humanized antibody directed against PD-1, or a combination thereof, and (ii) an immunomodulator, wherein said method results in enhanced therapeutic efficacy relative to administration of the check- point inhibitor or immunomodulator alone, wherein said immunomodulator comprises whole cell, non-pathogenic heat-killed *Mycobacterium obuense*, and wherein said whole cell, non-pathogenic heat-killed *Mycobacterium obuense* is administered to the subject prior to administering said checkpoint inhibitor.

2. The method according to claim 1, wherein said checkpoint inhibitor comprises atezolizumab, pembrolizumab, or a combination thereof.

3. The method according to claim 2, wherein said checkpoint inhibitor is pembrolizumab and wherein said patient has mismatch-repair deficient tumours and/or exhibits PD-L1 expression in at least 10%, or 20%, or 30%, or 40%, or 50% or more of tumour cells, as measured using the SP142 immunohistochemistry antibody assay.

4. The method according to claim 2, wherein said checkpoint inhibitor is atezolizumab, and wherein said atezolizumab is administered intravenously at a dose of at least 10 or 15 mg/kg or more every three weeks, optionally wherein said patient exhibits PD-L1 expression in at least 1%, 5% or 10% or more of tumour cells and/or tumour-infiltrating immune cells selected from B-cells and NK cells, as measured using the SP142 immunohistochemistry antibody assay.

5. The method according to claim 1, wherein said neoplasia, tumour or cancer is associated with a cancer selected from prostate cancer, liver cancer, renal cancer, lung cancer, breast cancer, colorectal cancer, breast cancer, pancreatic cancer, brain cancer, hepatocellular cancer, lymphoma, leukaemia, gastric cancer, cervical cancer, ovarian cancer, thyroid cancer, melanoma, carcinoma, head and neck cancer, skin cancer and soft tissue sarcoma.

6. The method according to claim 5, wherein said neoplasia, tumour or cancer is associated with pancreatic, colorectal, prostate or ovarian cancer.

7. The method according to claim 1, wherein said neoplasia, tumour or cancer is metastatic.

8. The method according to claim 1, wherein said whole cell, non-pathogenic heat-killed *Mycobacterium obuense* is the rough variant.

9. The method according to claim 8, wherein said whole cell, non-pathogenic heat-killed *Mycobacterium obuense* and/or checkpoint inhibitor is administered via the parenteral, oral, sublingual, nasal or pulmonary route.

10. The method according to claim 9, wherein the parenteral route is selected from subcutaneous, intradermal, subdermal, intraperitoneal, or intravenous.

11. The method according to claim 9, wherein the parenteral route comprises intratumoural injection.

12. The method according to claim 1, wherein the amount of whole cell, non-pathogenic heat-killed *Mycobacterium obuense* administered is from $10^7$ to $10^9$ cells.

13. The method according to claim 1, wherein the enhanced therapeutic efficacy is measured by increased overall survival time.

14. The method according to claim 1, wherein the enhanced therapeutic efficacy is measured by increased progression-free survival.

15. The method according to claim 1, wherein the enhanced therapeutic efficacy is measured by a decrease or stabilisation of tumour size.

16. The method according to claim 1, wherein the enhanced therapeutic efficacy is measured by an improved overall response rate and/or increased quality of life.

17. The method according to claim 1, wherein said checkpoint inhibitor comprises atezolizumab.

18. The method according to claim 1, wherein said checkpoint inhibitor comprises pembrolizumab.

* * * * *

UNITED STATES PATENT AND TRADEMARK OFFICE
CERTIFICATE OF CORRECTION

PATENT NO. : 11,207,405 B2
APPLICATION NO. : 15/738674
DATED : December 28, 2021
INVENTOR(S) : Akle et al.

Page 1 of 1

It is certified that error appears in the above-identified patent and that said Letters Patent is hereby corrected as shown below:

In the Claims

Column 19
Lines 28-29, "breast cancer, colorectal cancer, breast cancer, pancreatic cancer"
Should read:
--breast cancer, colorectal cancer, pancreatic cancer--

Signed and Sealed this
Twenty-second Day of February, 2022

Drew Hirshfeld
*Performing the Functions and Duties of the
Under Secretary of Commerce for Intellectual Property and
Director of the United States Patent and Trademark Office*